United States Patent
Teng

(10) Patent No.: US 9,230,701 B2
(45) Date of Patent: Jan. 5, 2016

(54) COLLIMATOR AND CT EQUIPMENT COMPRISING THE SAME

(75) Inventor: Chang Qing Teng, Shanghai (CN)

(73) Assignee: Siemens Shanghai Medical Equipment Ltd., Shanghai (CN)

( * ) Notice: Subject to any disclaimer, the term of this patent is extended or adjusted under 35 U.S.C. 154(b) by 296 days.

(21) Appl. No.: 13/823,457

(22) PCT Filed: Sep. 5, 2011

(86) PCT No.: PCT/EP2011/065256
§ 371 (c)(1),
(2), (4) Date: Mar. 14, 2013

(87) PCT Pub. No.: WO2012/034879
PCT Pub. Date: Mar. 22, 2012

(65) Prior Publication Data
US 2013/0177131 A1    Jul. 11, 2013

(30) Foreign Application Priority Data
Sep. 14, 2010    (CN) ........................ 2010 2 0527885 U

(51) Int. Cl.
G21K 1/02    (2006.01)
A61B 6/06    (2006.01)
A61B 6/00    (2006.01)
A61B 6/03    (2006.01)

(52) U.S. Cl.
CPC ... *G21K 1/02* (2013.01); *A61B 6/06* (2013.01); *A61B 6/4035* (2013.01); *A61B 6/035* (2013.01)

(58) Field of Classification Search
CPC ............ A61B 6/06; A61B 6/10; A61B 6/035; A61B 6/107; A61B 6/4035; B29K 2105/16; C08L 67/025; G21K 1/02; G21K 1/04

USPC ................................ 378/4, 147, 203; 359/641
See application file for complete search history.

(56) References Cited

U.S. PATENT DOCUMENTS

| | | | |
|---|---|---|---|
| 5,012,506 A * | 4/1991 | Span et al. ..................... | 378/152 |
| 2004/0022358 A1* | 2/2004 | Tomita ............................ | 378/70 |
| 2005/0025278 A1* | 2/2005 | Hagiwara ........................ | 378/7 |
| 2005/0025564 A1* | 2/2005 | Humpert et al. .............. | 403/282 |
| 2005/0152499 A1* | 7/2005 | Zhao et al. ..................... | 378/147 |
| 2008/0023636 A1* | 1/2008 | Chowdhury et al. ....... | 250/363.1 |
| 2010/0091378 A1 | 4/2010 | Norman et al. | |
| 2010/0111261 A1* | 5/2010 | Maack ........................... | 378/150 |

FOREIGN PATENT DOCUMENTS

| | | | | |
|---|---|---|---|---|
| DE | 102007028231 | | 1/2009 | |
| DE | 102007028231 A1 * | | 1/2009 | ............... H05G 1/02 |
| JP | 2003004892 | | 1/2003 | |

OTHER PUBLICATIONS

Machine translation of DE 102007028231 A1.*

* cited by examiner

*Primary Examiner* — Irakli Kiknadze
*Assistant Examiner* — Julio M Duarte-Carvajalino
(74) *Attorney, Agent, or Firm* — Schiff Hardin LLP

(57) ABSTRACT

An X-ray collimator has a collimation plate, and a shielding box made of a tungsten plastic composite, the shielding box having an opening on the top and the bottom thereof respectively, and a support part for supporting the shielding box. The collimation plate is disposed on the shielding box or the support part. Compared to the use of the shielding box alone, the collimator reduces the volume of the collimator without reducing its shielding performance.

14 Claims, 4 Drawing Sheets

COLLIMATOR AND CT EQUIPMENT COMPRISING THE SAME

BACKGROUND OF THE INVENTION

1. Field of the Invention

The present utility model relates to the technical field of the collimation of X-rays, and in particular to a collimator and to CT (X-ray computed tomography) equipment comprising the collimator.

2. Description of the Prior Art

In CT equipment, when the X-rays are emitted from an X-ray tube, they need to be collimated via a collimator before being radiated onto a subject to be examined, and then they are received by a detector. The main function of the collimator is to limit the X-rays to be a fan beam in the Z direction and in a ψ plane, and to shield the X-rays in other directions. The collimator is critical in protecting the patients and operators from receiving excessive doses of radiation.

FIGS. 1 and 2 are schematic diagrams of part of the structure of CT equipment, in which FIG. 1 shows a schematic diagram of a cross section of the CT equipment in the YZ plane, and FIG. 2 shows a schematic diagram of a cross section of the CT equipment in the XY plane. As shown in FIGS. 1 and 2, the CT equipment has an X-ray tube 100, a collimator 200, a patient bed 300 and a detector 400. An X-ray beam 500 emitted from the X-ray tube 100, after being collimated by the collimator 200, passes through a patient 600 lying on the patient bed 300, and then arrives at the detector 400. After receiving the X-rays, the detector 400 converts the X-ray intensity into electrical signals and transmits them to an image reconstruction device for reconstructing a CT image. Since the present application mainly relates to the collimator 200, other components of the CT equipment are not shown in the figures.

In the currently available collimators, lead is mainly used as the shielding material. However, lead is toxic which may cause damage to human bodies or the environment. The currently available collimators have been provided with sufficient protecting measures, and will cause no harm to a human body or the environment during their practical operation. Nevertheless, there is a strong desire to reduce and even eliminate the use of lead in collimators.

Currently, the shielding materials complying with the safety standards (for example, "the restriction of the use of certain hazardous substances in electrical and electronic equipment" (RoHS) of European Union) are rather expensive. Moreover, since a collimator is disposed on a narrow rotational part of the CT equipment, it is very difficult to replace lead with a large amount of light metal (such as steel), because it is necessary to use a large amount of light metal to achieve the same shielding performance but there is no space to accommodate so much light metal on the small rotational part.

Published German patent application DE102007028231A1 by Siemens discloses a collimator, in which a tungsten plastic composite is used as the shielding material of the collimator.

SUMMARY OF THE INVENTION

In view of the situation, an object of the invention is to provide a collimator that reduces the volume of the collimator without reducing its shielding performance. A further object is to provide CT equipment embodying such a collimator.

Accordingly, the present invention provides a collimator having a collimation plate, and the collimator further has:

a shielding box made of a tungsten plastic composite, which shielding box has an opening on the top and the bottom respectively;

a support part for supporting the shielding box;

with the collimation plate disposed on the shielding box or the support part.

Preferably, the shielding box has a cover plate and a box body; and the cover plate has an opening and the box body has an opening at the bottom.

Preferably, the box body is made by molding as one piece.

According to an embodiment, the thickness of the shielding box is 1.5-4.0 mm. Preferably, the thickness of the shielding box is uniform; or the bottom of the box body is the thickest, and the cover plate is the thinnest.

Preferably, the density of the tungsten plastic composite is 9-11 g/cm$^3$, or the tungsten content in said tungsten plastic composite is 94-96 wt %.

Preferably, the tungsten plastic composite is made by injection molding a mixture of tungsten and polycaprolactam.

According to an embodiment, the support part has a bottom plate, a cover plate, a side plate and a U-shaped plate; and the bottom plate and the cover plate each have an opening.

According to an embodiment, the support part is a combination of sheet metal parts and aluminum alloy machined parts.

Preferably, the collimator further has a fixed filter, which is located above the bottom opening of the shielding box and has a fixed connection to the shielding box.

According to an embodiment, the collimator further has at least one movable filter; a guide rail disposed on the shielding box, and by means of the guide rail, the movable filter can be moved to a position between the top opening and the bottom opening of the shielding box, or moved away from a position between the top opening and the bottom opening of the shielding box.

According to an embodiment, the collimation plate has a plate with a number of grooves. Alternatively, the collimation plate has a number of splints, which splints are movable by a motor, a screw rod or a linear electric motor disposed on the support part.

According to an embodiment, the collimator further has a pre-collimation plate that is disposed above the support part and has an opening corresponding to the top opening of the shielding box.

The present invention further encompasses CT equipment that includes such a collimator as described above, wherein the collimator is disposed on the rotational part of the CT equipment.

It can be seen from the above solution that since the collimator of the present invention is mainly designed as two parts of a shielding box and a support part, with the shielding box being used for shielding the reflected or scattered X-rays and the support part being used for providing the necessary strength and rigidity to support the shielding box. Since the material used by the support part is much less than that used by the shielding box for providing the same strength and rigidity, as compared to the use of the shielding box alone, the present invention reduces the volume of the collimator without reducing its shielding performance.

DESCRIPTION OF THE PREFERRED EMBODIMENTS

Figure 1:
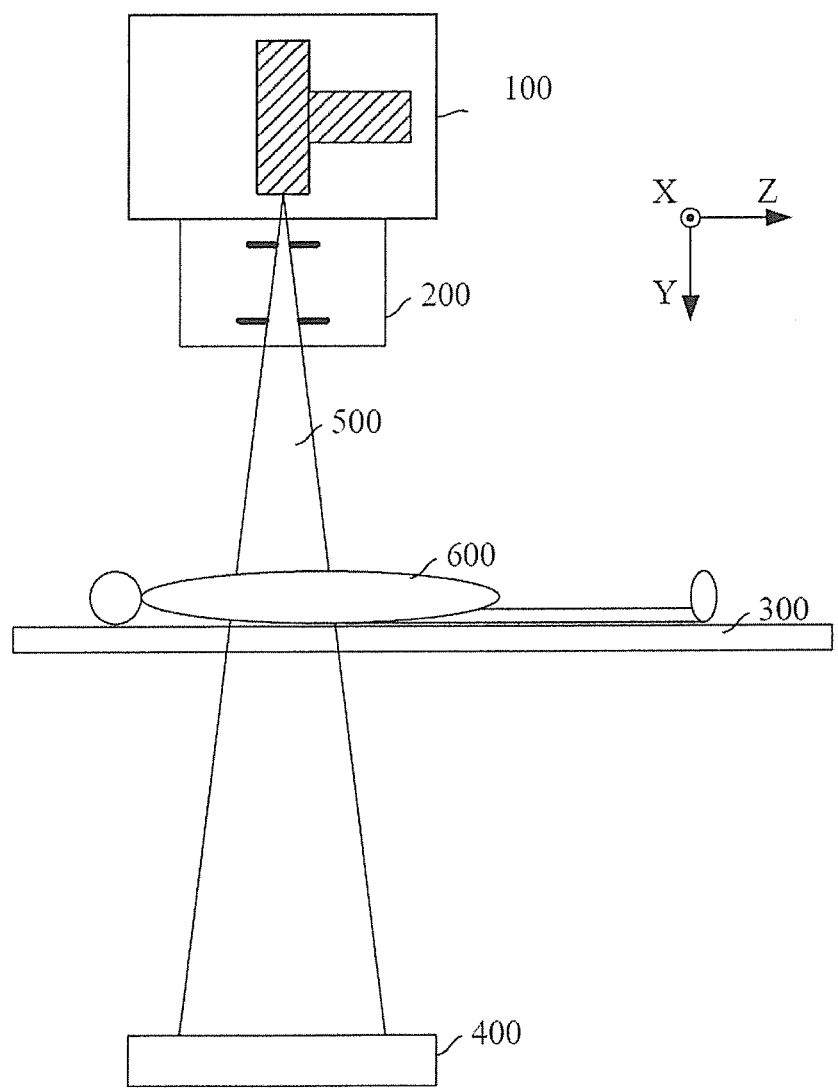
FIG. 1 is a schematic diagram of a cross section of CT equipment in the YZ plane.
Figure 2:
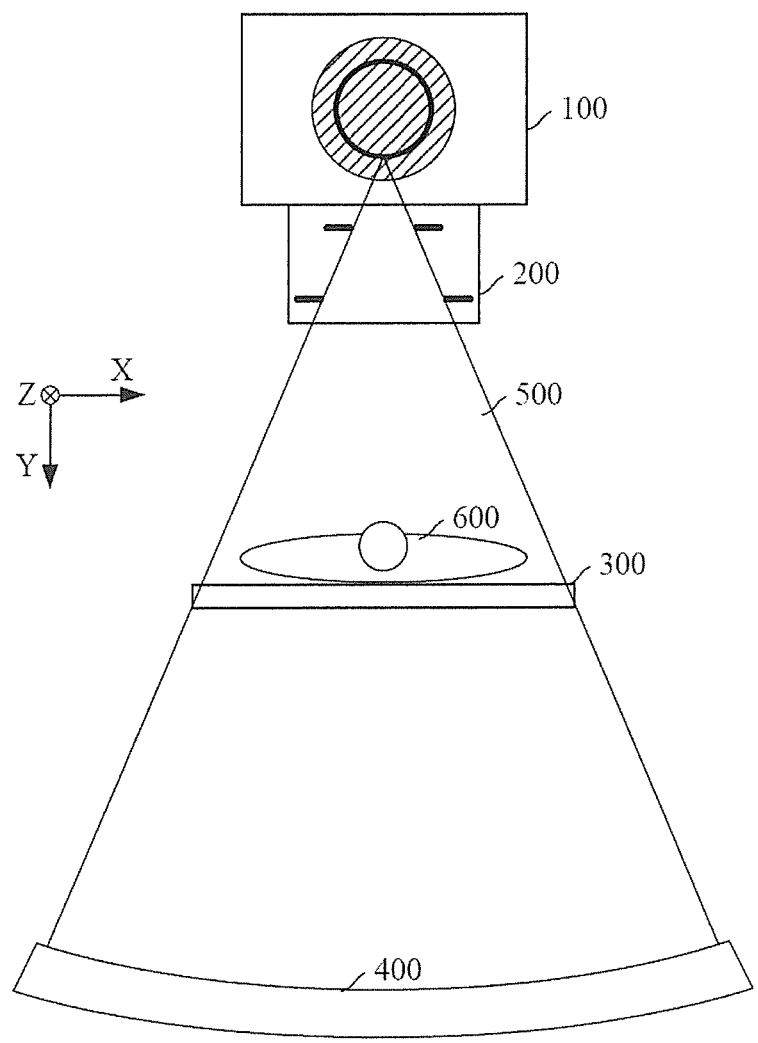
FIG. 2 is a schematic diagram of a cross section of the CT equipment in the XY plane.
Figure 3:
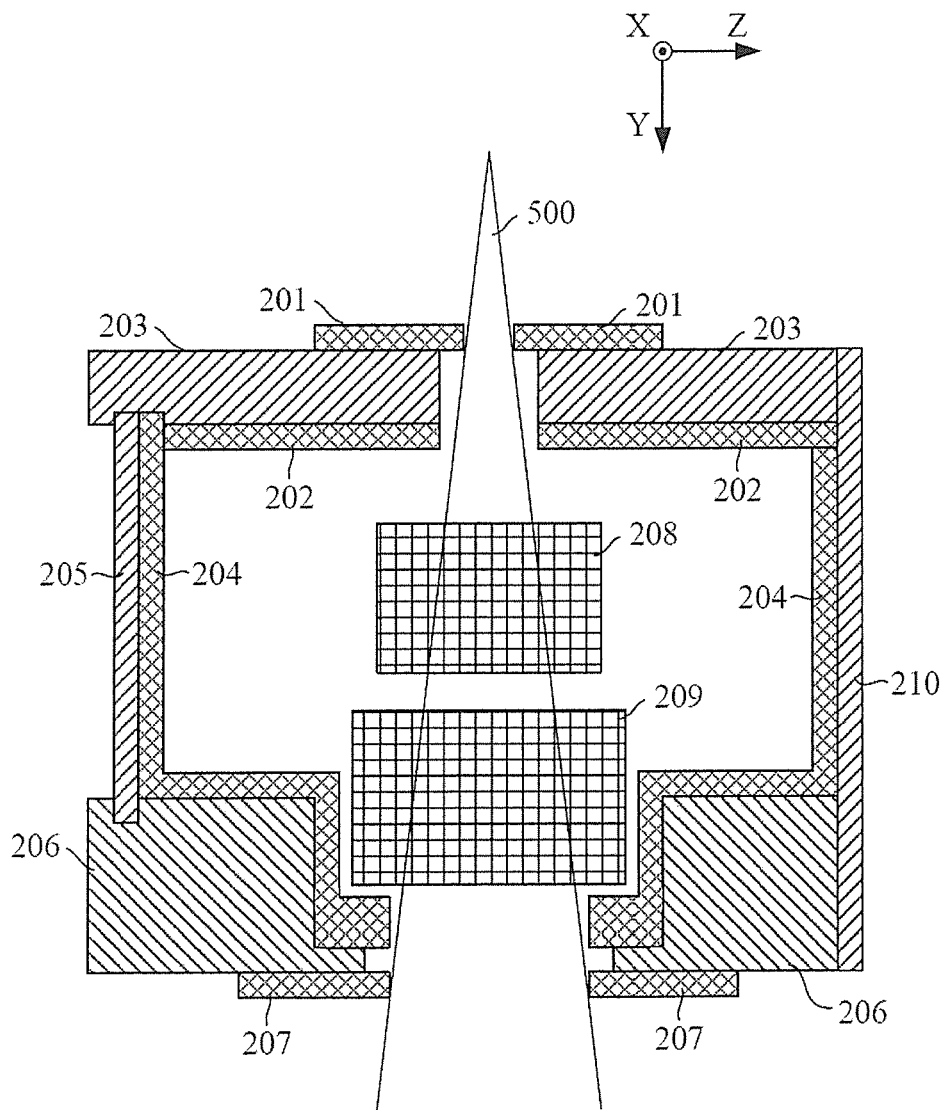
FIG. 3 is a schematic diagram of a cross section of a collimator according to an embodiment of the present invention in the YZ plane.
Figure 4:
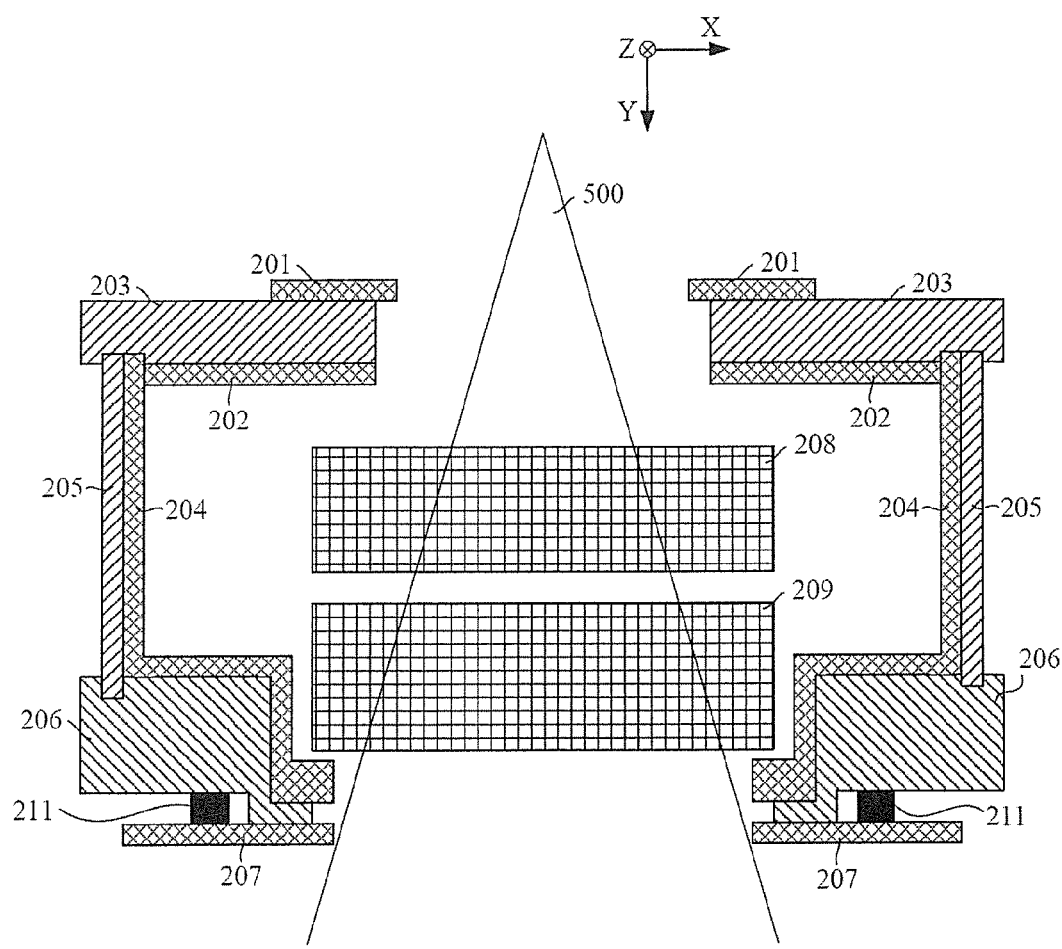
FIG. 4 is a schematic diagram of a cross section of a collimator according to an embodiment of the present invention in the XY plane.

FIGS. 3 and 4 show schematic diagrams of a collimator according to an embodiment of the present invention. In this case, FIG. 3 is a schematic diagram of a cross section of the collimator in the YZ plane, and FIG. 4 is a schematic diagram of a cross section of the collimator in the XY plane.

As shown in FIGS. 3 and 4, the collimator 200 according to an embodiment of the present invention is of a box-shape, and has a top opening and a bottom opening, and an X-ray beam 500 emitted from an X-ray tube 100 (not shown in the figure) passes through the top opening and the bottom opening to form a collimated X-ray beam.

As shown in the figure, the collimator 200 mainly comprises a collimation plate 207, a shielding box made of a tungsten plastic composite, and a support part for supporting the shielding box, which support part supports the shielding box from the exterior of the shielding box, and the support part can be connected to the shielding box by various ways such as screwing, welding, riveting, etc. The collimation plate 207 is used to collimate the X-ray beam 500 in the Z direction and in the XY plane (ψ plane).

The shielding box has an opening at the top for the X-ray beam to enter the collimator 200, and has an opening at the bottom for the X-ray beam to leave the collimator from this bottom opening.

It is well known that the shielding performance of a material is generally proportional to the density of the material, and the higher the density is, the better the shielding performance. Material with a high density is generally made of metal with a high atomic number. After comparison, the inventor of the present application has found out that tungsten is quite good a choice as the shielding material when considering factors such as whether it is economical or toxic. However, the use of pure tungsten or tungsten alloys will result in relatively high costs due to complicated manufacture process. The inventor has found out by research efforts that when using a tungsten plastic composite, a simple manufacture process can be employed with relatively low energy consumption and relatively high usage efficiency of the raw materials, so that the manufacturing costs can be reduced.

In the present invention, the density of the tungsten plastic composite for making the shielding box is about 9-11 g/cm$^3$. If the density is higher, a better shielding performance can be provided, however, the mechanical strength and rigidity of the tungsten plastic composite are reduced, for example, it would become more brittle and more fragile. By weight percentage, the tungsten content in the tungsten plastic composite is about 94-96 wt % (weight percent) and the remainder is plastic; and it is preferable to use plastics such as nylon-6 (polycaprolactam) and the like with a relatively high strength, relatively good elasticity and relatively high thermal deformation point. In order to ensure that the collimator would not deform due to high temperature during its use, the thermal deformation point of the tungsten plastic composite (preferably tungsten nylon composite) is greater than or equal to 70° C. It has been found out by comparison that the tungsten plastic composite used in the present application, as compared to lead, has a comparable shielding capacity and better mechanical performance.

The shielding box of the present invention can be manufactured by the following steps. First, tungsten powder is mixed with plastics, in which the tungsten particle diameter of the tungsten powder is less than 50 microns. In this step, the tungsten powder and the plastics need to be thoroughly and uniformly mixed. Then, they are made into a shielding box by injection molding. During the injection molding process, an injection pressure greater than or equal to 135 million pascals (MPa) is needed such that the tungsten plastic composite can be more uniform during the injection. Preferably, the position of the injection port is set such that the ratio (L/t) of the length (L) of the mixture passage from the injection port to the end of injection mold to the thickness (t) of the injection mold is less than or equal to 70. Preferably, a hot steam passage is disposed in the injection mold to maintain temperature so as to facilitate the mixing uniformity of the tungsten plastic mixture.

As shown in FIGS. 3 and 4, the shielding box comprises a cover plate 202 and a box body 204, in which the cover plate 202 has an opening for the X-rays to enter and the box body 204 has an opening at the bottom for the X-rays to leave. The box body can comprise a plurality of shielding plates and can be made by the combination of these shielding plates. Preferably, the box body 204 is made as one piece by the above injection molding means, so that X-ray leakage which may be present between the shielding plates can be avoided.

In the illustrated embodiment, the thickness of the shielding box is 1.5-4.0 mm. The thickness of each part of the shielding box can be uniform and can also be non-uniform. The present application is based on research showing that on the basis of the distribution of X-rays in the shielding box, the bottom of the shielding box can be preferably designed to be the thickest, then the side portion, with the top (cover plate 202) being the thinnest, so that the thickness of the shielding box is reduced without reducing its shielding performance.

As shown in FIGS. 3 and 4, the support part comprises a bottom plate 206, a side plate 210 and a U-shaped plate 205. These plates can be connected together by various ways such as screwing, welding, riveting, etc. The support part preferably uses a combination of sheet metal parts and aluminum alloy machine parts so that it is easy to manufacture.

The collimation plate 207 can be arranged on the shielding box (for example, the U-shaped plate 204), and can also be arranged on the support part (for example, a bottom plate 206). It might be as well to take the case that the collimation plate 207 is arranged on the bottom plate 206 as an example for the description of an embodiment of the present invention. The collimation plate 207 can be a plate with a number of grooves formed thereon, and by moving the collimation plate 207, the X-rays pass through different grooves so as to achieve different collimation effects. The collimation plate 207 can also have a plurality of (for example, 2) splints, and by setting the distance between the splints, X-ray beams with different sizes can be formed so as to achieve collimation. Preferably, a motor (for moving the collimation plate with the grooves) or a number of motors (for moving the splints respectively) (is) are disposed on the bottom plate 206. The motor or motors herein can be replaced with similar devices such as screw rods, linear electrical motors, etc.

As shown in the figures, the collimator 200 can have a fixed filter 209, which fixed filter 209 is disposed within the shielding box above the bottom opening, and connected to the shielding box. Preferably, the bottom of the box body 204 of the shielding box has a recess for accommodating the fixed filter 209. Correspondingly, the bottom plate 206 of the support part also has a recess. The fixed filter 209 is mainly used to filter low-energy X-rays.

More preferably, the collimator 200 can further have a movable filter 208, which movable filter 208 is disposed within the shielding box, above the fixed filter 209. The movable filter 208 is moved by a guide rail disposed on the box body 204 of the shielding box, and when the movable filter 208 is needed in use, it is moved to a position between the fixed filter 209 or the bottom opening of the shielding box and the top opening of the shielding box (above the X-ray beam 500), and when it is not needed, it is moved away from the above position and moved to one side of the shielding box (outside the X-ray beam 500). The movable filter 208 is mainly used to filter low-energy X-rays, so as to further enhance the filtering capacity of the collimator 200 and ensure that the energy of the X-rays is within the required range.

As shown in FIGS. 3 and 4, the collimator 200 can further have a pre-collimation plate 201. The pre-collimation plate 201 is disposed on the top plate 203 of the support part, and can be located outside the support part. The pre-collimation plate 201 is made by a high density alloy for pre-limiting the shape of the X-ray beams.

The CT equipment of the present invention comprises a collimator 200 as described above. The collimator 200 is disposed on the rotational part of the CT equipment.

Although modifications and changes may be suggested by those skilled in the art, it is the intention of the inventor to embody within the patent warranted heron all changes and modifications as reasonably and properly come within the scope of his contribution to the art.

The invention claimed is:

1. A collimator comprising:
   a collimation plate;
   a shielding box made of a tungsten plastic composite having a physical attribute that makes said shielding box brittle, said physical attribute being selected from the group consisting of a density of 9-11 g/cm$^3$, and a tungsten content of 94-96 wt %, the shielding box having an opening on each of a top and a bottom thereof;
   a support part that supports said shielding box by providing mechanical support to compensate the brittleness of the tungsten plastic composite; and
   said collimation plate being disposed on said shielding box or said support part.

2. The collimator according to claim 1, wherein said shielding box comprises a cover plate and a box body; said cover plate having an opening and said box body having an opening at the bottom.

3. The collimator according to claim 1, wherein thickness of said shielding box is 1.5-4.0 mm.

4. The collimator according to claim 1, wherein a thickness of said shielding box is uniform; or the bottom of the box body of said shielding box is thickest and the cover plate is thinnest.

5. The collimator according to claim 1 wherein said tungsten plastic composite is made by the injection molding of tungsten and polycaprolactam.

6. The collimator according to claim 1, wherein said support part comprises a bottom plate, a cover plate, a side plate and a U-shaped plate, said bottom plate and said cover plate each have an opening.

7. The collimator according to claim 1, wherein said support part is a combination of a sheet metal part and an aluminum alloy machined part.

8. The collimator according to claim 1, further comprising a fixed filter located above the bottom opening of said shielding box and fixedly connected to said shielding box.

9. The collimator according to claim 1, further comprising at least one movable filter; and
   a guide rail disposed on said shielding box, and by means of said guide rail said movable filter is moved into a position between the top opening and the bottom opening of said shielding box, or moved away from its position between the top opening and the bottom opening of said shielding box.

10. The collimator according to claim 1, wherein said collimation plate comprises a plate with a plurality of grooves;
    or said collimation plate comprises a plurality of splints, which splints are moved by a motor, a screw rod or a linear electric motor disposed on the support part.

11. The collimator according to claim 1, further comprising a pre-collimation plate disposed above said support part, said pre-collimation plate having an opening corresponding to the top opening of said shielding box.

12. A computed tomography apparatus, comprising:
    a computed tomography data acquisition unit comprising an X-ray source that emits an X-ray beam that is rotatable around an axis, and a radiation detector on which said x-ray beam is incident after attenuation by an object, said radiation detector emitting detector signals, and a processor configured to execute an algorithm to reconstruct a computed tomography image from detector signals received with said X-ray beam at respectively different angular positions around said axis; and
    a collimator mounted to collimate said x-ray beam before said x-ray beam reaches said object, said collimator comprising a collimator plate, a shielding box made of a tungsten plastic composite having a physical attribute that makes said shielding box brittle, said physical attribute being selected from the group consisting of a density of 9-11 g/cm$^3$, and a tungsten content of 94-96 wt %, said shielding box having an opening in each of a top and a bottom thereof, a support part that supports said shielding box by providing mechanical support to compensate the brittleness of the tungsten plastic composite, and said collimator plate being disposed in said shielding box or said support part.

13. A collimator comprising:
    a collimation plate;
    a shielding box made of a tungsten plastic composite, the shielding box having an opening on each of a top and a bottom thereof;
    a support part that supports said shielding box;
    said collimation plate being disposed on said shielding box or said support part; and
    a guiderail disposed on said shielding box, and by means of said guiderail, a movable filter being movable into a position between the top opening and the bottom opening of the shielding box, or away from a position between the top opening and the bottom opening of said shielding box.

14. A computed tomography apparatus, comprising:
    a computed tomography data acquisition unit comprising an X-ray source that emits an X-ray beam that is rotatable around an axis, and a radiation detector on which said x-ray beam is incident after attenuation by an object, said radiation detector emitting detector signals, and a processor configured to execute an algorithm to reconstruct a computed tomography image from detector signals received with said X-ray beam at respectively different angular positions around said axis;

a collimator mounted to collimate said x-ray beam before said x-ray beam reaches said object, said collimator comprising a collimator plate, a shielding box made of a tungsten plastic composite having a physical attribute that makes said shielding box brittle, said shielding box having an opening in each of a top and a bottom thereof, a support part that supports said shielding box by providing mechanical support to compensate the brittleness of the tungsten plastic composite, and said collimator plate being disposed in said shielding box or said support part; and a guiderail disposed on said shielding box, and by means of said guiderail, a movable filter being movable into a position between the top opening and the bottom opening of the shielding box, or away from a position between the top opening and the bottom opening of said shielding box.

* * * * *